(12) United States Patent
Mordon et al.

(10) Patent No.: US 6,562,025 B2
(45) Date of Patent: *May 13, 2003

(54) APPARATUS FOR UNITING THE LIPS OF A WOUND, A HOLDING PIECE, AND A COSMETIC TREATMENT METHOD

(75) Inventors: Serge R. Mordon, Villeneuve d'Ascq (FR); Alexandre Capon, Lesquin (FR); Chryslain Sumian, Antibes (FR)

(73) Assignee: Galderma Research & Development, S.N.C., Sophia Antipolis (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/358,438

(22) Filed: Jul. 22, 1999

(65) Prior Publication Data
US 2002/0111609 A1 Aug. 15, 2002

(30) Foreign Application Priority Data
Jul. 27, 1998 (FR) .............................................. 98 09557

(51) Int. Cl.[7] .............................................. A61B 18/18
(52) U.S. Cl. ............................ 606/8; 606/151; 606/213
(58) Field of Search .......................... 606/8–9, 13, 2–3, 606/11, 16; 128/888–889

(56) References Cited

U.S. PATENT DOCUMENTS

| | | | | |
|---|---|---|---|---|
| 4,672,969 A | * | 6/1987 | Dew | 128/397 |
| 5,300,065 A | * | 4/1994 | Anderson | 606/13 |
| 5,569,239 A | * | 10/1996 | Sinofsky | 128/898 |
| 5,643,252 A | * | 7/1997 | Waner et al. | 604/21 |
| 5,662,643 A | * | 9/1997 | Kung et al. | 606/3 |
| 5,725,522 A | * | 3/1998 | Sinofsky | 606/8 |
| 5,749,895 A | * | 5/1998 | Sawyer et al. | 606/214 |
| 6,156,028 A | * | 12/2000 | Prescott | 606/2 |

OTHER PUBLICATIONS

Suzanne L. Kilmer et al., "Clinical Use of the Q–Switched Ruby and the Q–Switched Nd;YAG (1064 nm and 532 nm) Lasers for Treatment of Tattoos", *Journal of Dermatologic Surgery and Oncology*, 1993, 19:330–338.

* cited by examiner

Primary Examiner—Michael Peffley
(74) Attorney, Agent, or Firm—Oliff & Berridge, PLC

(57) ABSTRACT

The apparatus for uniting the lips of a wound comprises a laser having an emission wavelength chosen such that it can perform tissue bonding and unite the lips of a wound, and a holding piece suitable for being secured to the tissue around the wound so as to keep the lips of the wound approximated, at least while the wound is being exposed to said laser radiation, the holding piece including at least one region suitable for being positioned over the wound and sufficiently transparent at the wavelength of the laser radiation for the energy from said radiation to be sufficient, after it has passed through said region, to perform the desired tissue bonding.

20 Claims, 1 Drawing Sheet

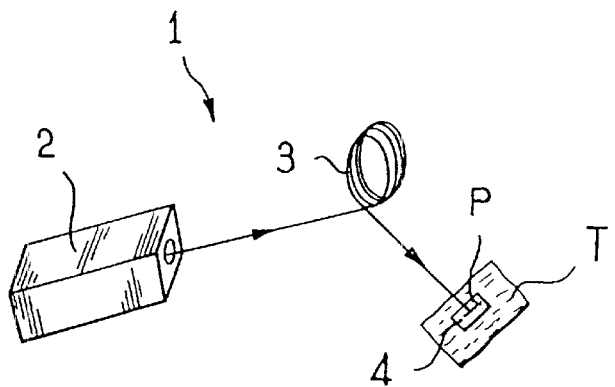
FIG_1
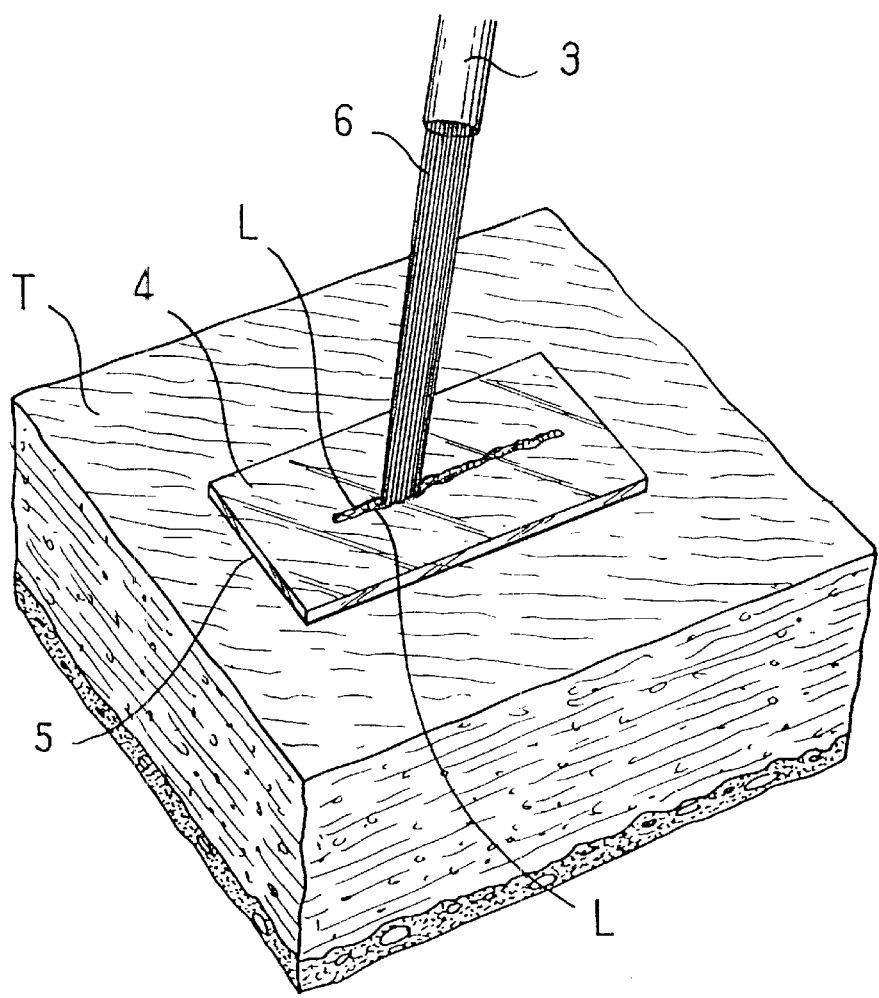
FIG_2

APPARATUS FOR UNITING THE LIPS OF A WOUND, A HOLDING PIECE, AND A COSMETIC TREATMENT METHOD

The present invention relates to closing a wound, in particular a cutaneous wound.

BACKGROUND OF THE INVENTION

Suturing the skin by commonly-used techniques employing thread or clips, is a relatively lengthy and tiresome task, and it involves non-negligible risks of scarring, in particular the risk that a hypertrophic scar might form.

There has long been a need to find means for closing wounds rapidly without using foreign bodies such as threads or clips, while obtaining scars that are strong and of identical or even better quality.

Bonding skin together by laser has been proposed as an alternative to suturing with thread or clips.

Unfortunately, it has been found that wounds closed using such bonding have very low traction strength during the first few days of the healing process, so that they are likely to re-open.

Attempts have been made to remedy that drawback by performing the laser irradiation in the presence of a dye chosen to increase the amount of radiation absorbed by the tissue in which the wound is situated.

Unfortunately, the use of such a dye raises difficulties associated with the quantity of dye deposited and with the reproducibility of deposition.

Proposals have also been made to use adhesives based on fibrin or on proteins, in particular human albumin serum, those adhesives being intended to impart greater strength to the closure.

Unfortunately, adding exogenous substances of human origin or of animal origin raises problems of tolerance and involves the risk of transmitting viral or spongiform diseases.

OBJECTS AND SUMMARY OF THE INVENTION

An object of the present invention is to provide apparatus for uniting the lips of a wound, which apparatus offers an alternative to suturing tissue by commonly-used techniques employing thread or clips, without suffering from the drawbacks associated with adding an exogenous substance or a foreign body.

The apparatus of the invention comprises a laser having an emission wavelength chosen such that it can perform tissue bonding and unite the lips of a wound, and a holding piece suitable for being secured to the tissue around the wound so as to keep the lips of the wound approximated, at least while the wound is being exposed to said laser radiation, the holding piece including at least one region suitable for being positioned over the wound and sufficiently transparent at the wavelength of the laser radiation for the energy from said radiation to be sufficient, after it has passed through said region, to perform the desired tissue bonding.

By means of the invention, the wound is closed well because the holding piece prevents any disuniting of the lips during the healing process.

In particular, the apparatus of the invention makes it possible to ensure that the lips are held together properly approximated during the laser irradiation.

By means of the invention, the healing takes place correctly and rapidly.

In addition, the invention makes it possible to reduce the time required for the surgeon to close the wound, compared with conventional suturing using thread.

In a particular embodiment, the holding piece is flexible, and is preferably in the form of an adhesive strip.

Also in a particular embodiment, the holding piece incorporates one or more substances promoting healing and/or having an antiseptic effect.

Preferably, these substances are chosen such that they have no direct activity on the conversion of light into heat, which could be detrimental to the desired healing process.

Advantageously, in its zone covering the wound, the holding piece includes at least one region whose absorption coefficient at the wavelength of the laser radiation used is chosen such that the quantity of energy absorbed by said holding piece is not more than 50% of the incident energy, and preferably is less than 20% of said incident energy.

For example, the wavelength of the laser radiation used is chosen from the following values or ranges of values: 800 nm to 980 nm; 1.06 $\mu$m to 1.32 $\mu$m; 0.514 $\mu$m; 2.9 $\mu$m; 10.6 $\mu$m; and 0.805 $\mu$m; and preferably from the following values: 810 nm; 980 nm; 1.55 $\mu$m; and 532 nm.

The invention also provides a holding piece as defined above.

The invention also provides a method of closing a wound, said method comprising the following steps:

approximating the lips of the wound, and sticking a holding piece on the tissue across the wound, thereby covering the wound and keeping the lips of said wound approximated; and uniting the lips of the wound by performing tissue bonding by means of laser radiation through the holding piece, the holding piece being sufficiently transparent at the wavelength of the laser radiation for the energy from said radiation to be sufficient, after it has passed through said region, to perform the desired tissue bonding.

Preferably, the holding piece is left on the wound after the laser radiation treatment for at least two days, and preferably for a period lying in the range two days to seven days.

The invention also provides the use of apparatus as defined above for uniting the lips of a wound during an operation, in particular a cosmetic surgery operation.

The invention also provides a method of cosmetically treating the skin, the method making it possible to reduce the risks of an ugly scar forming during healing of a wound, said method comprising the following steps:

applying a holding piece as defined above against the skin; and irradiating the skin through said holding piece by means of a laser as defined above.

The invention also provides a holding piece designed to be used in surgical laser treatment by being applied against tissue around the lips of a wound so as to hold them in a predetermined position at least during the exposure to laser radiation.

BRIEF DESCRIPTION OF THE DRAWING

The invention will be better understood on reading the following description of a non-limiting embodiment and on examining the accompanying drawing, in which:

FIG. 1 is a diagrammatic view of an embodiment of the apparatus of the invention; and FIG. 2 is a diagrammatic view showing how the wound is irradiated through the holding piece.

MORE DETAILED DESCRIPTION

As shown in FIG. 1, the apparatus 1 for uniting the lips of a wound P comprises firstly a laser 2 that can be associated with light-guiding means comprising an optical fiber 3 for guiding the radiation emitted by the laser and directing it towards the wound P, and secondly a holding piece 4 designed to be applied temporarily against the tissue T, constituted in the example described by skin, so as to cover the wound P.

The use of an optical fiber 3 is not essential, and it is also possible to project the laser radiation 2 from the laser 2 directly onto the wound, or else to direct the laser radiation 2 onto one or more steerable mirrors.

For example, the laser used may be a $CO_2$ laser emitting radiation of wavelength 10.6 $\mu$m, an Nd:YAG laser emitting in a wavelength range 1.06 $\mu$m to 1.32 $\mu$m, an argon laser emitting at a wavelength of 0.514 $\mu$m, an erbium laser emitting at 1.55 $\mu$m or 2.9 $\mu$m, or a laser diode emitting in the range 800 nm to 980 nm, or else a frequency-doubled Nd:YAC laser emitting at 532 nm, this list naturally not being limiting.

Preferably, use is made of a laser diode emitting in the range 800 nm to 980 nm, or of an Nd:YAG laser emitting in the wavelength range 1.06 $\mu$m to 1.32 $\mu$m.

In general, the wavelength of the laser radiation is chosen in a manner such that it is possible to bond the tissue, thereby uniting the lips L of the wound P.

In the embodiment described, the holding piece 4 is constituted by a flexible strip having an adhesive face 5 so that it can adhere to the skin around the wound P to be closed.

In the embodiment described, the strip 4 is made of a plastics material that is transparent to the wavelength of the laser radiation 6 emitted at the outlet of the light-guiding means 3.

Without going beyond the ambit of the present invention, it is also possible to use a strip 4 made of a textile material, for example.

In the present invention, the term "transparent" is used to mean that the strip 4 absorbs the radiation 6 to an extent small enough so that, after it has passed through the strip 4, the laser radiation 6 has enough energy to bond the tissue in the desired manner.

In the example described, the strip 4 is advantageously constituted by a polyurethane film covered with a layer of acrylic adhesive.

For example, the apparatus 1 may be used as follows.

The strip 4 is applied against the skin progressively, by unrolling it from one end to the other while holding the lips L approximated locally.

Preferably, the length of the strip 4 used is greater than the length of the wound P, as shown in FIG. 2.

Then the lips L of the wound are united by bonding the tissue by means of the laser radiation 6.

The energy to be provided to perform the tissue bonding, and the location of the point of impact of the laser radiation on the tissue are elements that are easy for the user to determine as a function of the result to be obtained.

In the example described, the laser radiation 6 is applied continuously along the wound so as to unite the lips L over their entire length.

In a variant, the laser radiation may be applied discontinuously, by performing successive irradiation operations with the points of impact being touching or slightly overlapping.

Once the lips L have been united, the strip 4 is left in place for at least two days so as to prevent any disuniting of the lips L under the effect of any traction exerted on the skin.

Preferably, the strip 4 contains active substances making it possible to accelerate the healing process as well as antiseptic substances such as iodine if necessary.

Preferably, the strip 4 is made of a material which allows the laser radiation to pass through it substantially without diffusing it or diffracting it, so as not to hinder focusing said radiation onto a desired point of the wound.

Also preferably, the strip 4 is transparent not only to the laser radiation used, but also to visible radiation, so as to enable the surgeon to see the tissue bonding operation clearly through the strip 4 and then to inspect the healing process to ensure that it is taking place properly.

Satisfactory trials have been made using a laser diode emitting at 810 nm, and holding pieces constituted by adhesive dressings sold under the names Tegaderm, Opsite, and Visulin, and which respectively allow 88%, 96%, and 94% of the laser radiation to pass through them.

Naturally, the invention is not limited to the above-described embodiment.

In particular, it is possible to use holding pieces that are of various shapes.

Thus, in a variant embodiment (not shown) a holding piece is used that has perforations between bridges of material serving to hold the lips during the tissue bonding operation, and subsequently.

The tissue bonding is then performed by laser irradiation via said perforations.

In this variant embodiment, outside said perforations, the holding piece may thus be made of a material that is not transparent to the laser radiation used, if it is acceptable for the tissue bonding to be discontinuous because of the presence of said bridges of material between the perforations.

Finally, the invention makes it possible to reduce the risk of infection, since the holding piece can provide additional protection against bacteria, and it is possible to obtain very good results in terms of appearance.

In addition, the invention makes it possible to reduce operating time considerably.

The wound-closing time can be reduced by a factor of three or four.

By way of example, during the trials that have been conducted, the wound-closing time was reduced to one and one half minutes instead of six minutes with conventional thread suturing.

The invention also makes it possible to obtain good results in terms of healing speed.

What is claimed is:

1. A method of closing a wound, comprising
   approximating the lips of the wound and sticking on the tissue across the wound a holding piece having an adhesive layer permanently attached thereto, thereby covering the wound and keeping the lips of said wound approximated; and
   uniting the lips of the wound by performing tissue bonding by laser radiation through the holding piece, the holding piece having a region sufficiently transparent at the wavelength of the laser radiation for the energy from said radiation to be sufficient, after it has passed through said region, to perform the desired tissue bonding.

2. A method according to claim 1, wherein said holding piece is flexible.

3. A method according to claim 1, wherein the holding piece is in the form of an adhesive strip.

4. A method according to claim 1, wherein said holding piece is made of a film of plastics material covered with a layer of adhesive.

5. A method according to claim 1, wherein said film is made of polyurethane.

6. A method according to claim 1, wherein said adhesive is an acrylic adhesive.

7. A method according to claim 1, wherein said holding piece incorporates at least one substance promoting healing.

8. A method according to claim 1, wherein said holding piece incorporates at least one substance having an antiseptic effect.

9. A method according to claim 1, wherein said holding piece incorporates at least one substance promoting healing and having an antiseptic effect.

10. A method according to claim 1, wherein, in its zone covering the wound, the holding piece includes at least one region whose absorption coefficient at the wavelength of the laser radiation used is chosen such that the quantity of energy absorbed by said holding piece is less than 50% of the incident energy.

11. A method according to claim 1, wherein the quantity of energy absorbed by said holding piece is less than 20% of said incident energy.

12. A method according to claim 1, wherein the wavelength of the laser radiation used is selected from the following values or ranges of values: 800 nm to 980 nm; 10.6 $\mu$m; 1.06 $\mu$m to 1.32 $\mu$m; 0.514 $\mu$m; and 2.9 $\mu$m.

13. A method according to claim 1, wherein the wavelength of the laser radiation is selected from the following values: 810 nm; 980 nm; 1,55 $\mu$m and 532 $\mu$m.

14. A method according to claim 1, wherein the holding piece is left on the skin for at least two days.

15. A method according to claim 1, wherein the holding piece is left on the skin for a period lying in the range two days to seven days.

16. A method according to claim 1, wherein the laser radiation is applied continuously along the wound.

17. A method according to claim 1, wherein the laser radiation is applied discontinuously, by performing successive irradiation operations with the points of impact being touching or slightly overlapping.

18. A method according to claim 1, wherein the holding piece incorporates at least one substance having no direct activity on the conversion of light into heat.

19. A method according to claim 1, wherein the holding piece is transparent over its whole surface at the wavelength of the laser radiation.

20. A method according to claim 1, wherein the holding piece has an adhesive layer covering entirely a face thereof.

* * * * *